United States Patent [19]
Takeda et al.

[11] Patent Number: 6,153,185
[45] Date of Patent: *Nov. 28, 2000

[54] PLANT-CONTAINING COMPOSITION

[75] Inventors: Minoru Takeda, Tokyo; Hirotaka Tagoshi, Chiba; Susumu Tago, Miyagi, all of Japan

[73] Assignee: Showa Denko Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/041,617

[22] Filed: Mar. 13, 1998

[30] Foreign Application Priority Data

Mar. 13, 1997 [JP] Japan .................................... 9-078840
Sep. 1, 1997 [JP] Japan .................................... 9-251396

[51] Int. Cl.$^7$ ............................ A01H 11/00; A01G 31/00
[52] U.S. Cl. ........................ 424/93.7; 504/150; 424/93.1; 524/916
[58] Field of Search .................................... 504/113, 114, 504/116, 150; 424/93.7

[56] References Cited

U.S. PATENT DOCUMENTS 3,336,129  8/1967  Herrett et al. .......................... 504/116
4,985,061  1/1991  Hughes .................................... 504/114
5,185,024  2/1993  Siemer et al. .......................... 504/116

FOREIGN PATENT DOCUMENTS 8-256592  8/1996  Japan .

OTHER PUBLICATIONS

Patent Abstracts of Japan, vol. 097, No. 002, Feb. 28, 1997 & JP 08 256592 A... Class A14, Derwent Publications Ltd., London, GB; Class A14, AN 96–500196.

Primary Examiner—Peter F. Kulkosky
Attorney, Agent, or Firm—Sughrue, Mion, Zinn, Macpeak & Seas, PLLC

[57] ABSTRACT

Disclosed is a composition comprising a plant capable of growing in the presence of at least water and light, a nonionic water-absorptive polymer, and water, and a method of use of the composition as well as a method of fabricating a revegetation material.

6 Claims, 7 Drawing Sheets

(7 of 7 Drawing Sheet(s) Filed in Color)

PLANT-CONTAINING COMPOSITION

BACKGROUND OF THE INVENTION

1. Field of the Invention

The present invention relates to a composition comprising a plant and a specific polymer having water absorbing properties that contains water, which composition enables the plant to grow therein. More particularly, the present invention relates to a composition which enables continuous growth therein of a plant which is able to grow in the presence of at least water and light, by having the plant coexist with a nonionic water-absorptive polymer which absorbs at least water, particularly N-vinyl carboxylic amide polymer, more particularly N-vinyl acetamide polymer.

2. Description of the Related Art

As is well known, the consumption of fossil fuels, typified by petroleum and coal, has recently been increasing drastically due to human activities, resulting in a rapid increase in carbon dioxide concentration in the atmosphere.

The balance in the amounts of atmospheric oxygen and carbon dioxide has mainly been preserved by plant resources. However, this balance is being lost by the drastic increase in carbon dioxide due to deforestation as well as the aformentioned circumstances.

It is predicted that the drastic increase in carbon dioxide in the atmosphere will greatly affect the earth's climate in the near future due to the so-called greenhouse effect.

Throughout the world, there have been made attempts to slow down the increase in atmospheric carbon dioxide concentration, such as control of automobile emissions and preservation and improvement of the environment, including forests, but none of these attempts have succeeded.

As mentioned above, plant resources are the primary factor in preserving the balance in the amounts of atmospheric oxygen and carbon dioxide, but the consumption of forest resources is unavoidable in the maintenance of civilization as we know it. Therefore, indiscriminate deforestation has continued unabatedly and recovery of forest resources is far from catching up with deforestation.

In view of the foregoing, relatively lower plants such as phytoplankton, marine plants, and Bryophyta are of interest.

First, lower plants provide excellent absorption efficiency of carbon dioxide because, unlike the tree, they don't have large bodies consisting of cellulosic skeletons. Secondly, these plants are considered suitable for bulk use in factories and plant facilities where large amounts of carbon dioxide are produced. Also, unlike terrestrial plants, many of these plants have an advantage in that they can grow in harsh environments.

Accordingly, there have been made various attempts to use the aforementioned phytoplankton and the like having these properties as a means to recover the balance in the amounts of atmospheric oxygen and carbon dioxide. However, none of the attempts have been put into full-scale practical use, because growing the aforementioned phytoplankton and the like continuously and having them perform photosynthesis efficiently would require large-scale facilities which permit continuous stirring.

In order to realize recovery of the balance in the amounts of atmospheric oxygen and carbon dioxide by use of the aforementioned plants, there must be provided a means to collect as much phytoplankton and the like as possible and to have them perform photosynthesis efficiently.

One plausible means for this is to immobilize the aforementioned phytoplankton alive. This immobilization requires a carrier which permits immobilization of the aforementioned phytoplankton alive.

As a carrier for this immobilization, mention is given first of water-absorptive polymers.

Water-absorptive polymers are currently classified into three classes; i.e. starch, cellulosic, and synthetic polymers, and all these provide excellent water absorbing abilities.

However, when water-absorptive polymers are caused to absorb water and then are permitted to come into contact with phytoplankton and the like, none of the polymers are able to grow the phytoplankton and the like continuously, letting the phytoplankton and the like be killed in a short time.

SUMMARY OF THE INVENTION

Accordingly, an object of the present invention is to provide means for immobilization of the aforementioned phytoplankton and the like which enables their continuous growth.

The present inventors have carried out extensive studies in an attempt to resolve the above-mentioned problems, and, focusing on synthetic, nonionic water-absorptive polymers among numerous other water-absorptive polymers, they have studied their characteristics as plant-immobilizing carriers. As a result, the inventors have made the surprising discovery that when nonionic water-absorptive polymers, inter alia N-vinylcarboxylic amide polymers, and more specifically N-vinylacetamide polymer, are caused to absorb water and are used for immobilizing phytoplankton or the like, the phytoplankton or the like grow continuously in the polymers without causing pollution due to germs even after being left to stand over one year. The present invention was accomplished based on this finding.

Also, even more surprisingly, the present inventors found that when the polymer and water are brought into contact to form a hydrogel aggregate and the kinetic viscosity of the hydrogel aggregate is adjusted to 500 Stokes or less at ambient temperature, and this low-viscosity hydrogel aggregate is allowed to stand after having been mixed with phytoplankton or the like, the phytoplankton or the like don't float on the low-viscosity hydrogel aggregate, sediment therein, or adhere to the walls of the vessel, but they maintain the uniformly dispersed state and grow continuously for prolonged periods.

Accordingly, the present inventors provide the following inventions as disclosed herein.

In a first aspect of the present invention, there is provided a composition comprising a plant capable of growing in the presence of at least water and light, a nonionic water-absorptive polymer, and water.

In the composition of the present invention, the nonionic water-absorptive polymer is preferably a N-vinylcarboxylic amide polymer derived from a monomer containing 50% by weight or more of N-vinylcarboxylic amide represented by the following formula (I):

$$CH_2=CHNR^1COR^2 \qquad (I)$$

wherein $R^1$ and $R^2$, which may be identical to or different from each other, represent a hydrogen atom or a lower alkyl group, for example, a methyl group, an ethyl group, an n-propyl group, or an isopropyl group, or $R^1$ and $R^2$ are linked to each other to form a group —$C_3H_6$—.

In a second aspect of the present invention, there is provided a method of use of an N-vinylcarboxylic amide polymer, comprising incorporating, into a hydrogel aggeregate obtained by contacting an N-vinylcarboxylic amide polymer and water, a plant capable of growing in the presence of at least water and light, to thereby continuously grow the plant, the N-vinylcarboxylic amide polymer being derived from a monomer containing 50% by weight or more of N-vinylcarboxylic amide represented by the following formula (I):

$$CH_2=CHNR^1COR^2 \quad (I)$$

wherein $R^1$ and $R^2$, which may be identical to or different from each other, represent a hydrogen atom or a lower alkyl group, for example, a methyl group, an ethyl group, an n-propyl group, or an isopropyl group, or $R^1$ and $R^2$ are linked to each other to form a group $-C_3H_6-$.

In a third aspect of the present invention, there is provided a method of use of a composition containing a plant capable of growing in the presence of at least water and light, a nonionic water-absorptive polymer, and water, as a means for cultivating the plant.

In a fourth aspect of the present invention, there is provided a method for producing a revegetation material, the method comprising placing, in a container formed of a waterproof material and having ventilation means, a composition containing at least one plant selected from the group consisting of algae, Bryophyta, and Lichenes; and a nonionic water-absorptive polymer, and water, so as to cultivate the plant contained in the composition, allowing to moss bodies to intertwine within the cultivation system, and subsequently removing the nonionic water-absorptive polymer from the cultivation system.

In the present invention, the N-vinylcarboxylic amide polymer derived from a monomer containing 50% by weight or more of N-vinylcarboxylic amide represented by formula (I) is preferably a crosslinked polymer, more preferably, a copolymer containing 70% by weight or more of N-vinylcarboxylic amide represented by formula (I).

Particularly preferably, N-vinylcarboxylic amide is N-vinylacetamide, which is represented by formula (I) in which $R^1$ is a hydrogen atom and $R^2$ is a methyl group.

In the present invention, the plant capable of growing in the presence of at least water and light is preferably at least one plant selected from the group consisting of algae, Bryophyta, and Lichenes. Of these, algae may be freshwater algae or seawater algae.

The composition and the hydrogel aggregate of the present invention has a kinetic viscosity of either at least 500 Stokes or less than 500 Stokes at ambient temperature.

The term "kinetic viscosity" as used herein refers to a viscosity measured by use of an air bubble viscometer manufacture by Gardner Co. Ltd. With this type of a viscometer, the "kinetic viscosity" is measured as follows. First, a test tube having an inner diameter of 1.065 cm is filled with a sample until the sample reaches the level that leaves space of 0.8 cm high, and the test tube is sealed with a plug. The test tube is subsequently placed upside down and the rising speed of the bubble is observed. The thus-obtained bubble-rising speed is compared with corresponding values of standard samples whose kinetic viscosities are known, to thereby determine the kinetic viscosity of the test sample.

BRIEF DESCRIPTION OF THE DRAWINGS

The file of this patent contains 14 drawings executed in color. Copies of this patent with color drawing(s) will be provided by the Patent and Trademark Office upon request and payment of the necessary fee.

DETAILED DESCRIPTION OF PREFERRED EMBODIMENTS

The present invention will next be described in detail. A. The composition of the present invention is a composition comprising a nonionic water-absorptive polymer as an essential component.

The nonionic water-absorptive polymer, which is an essential component of the composition of the present invention, is not particularly limited, and there may be employed synthetic polymers such as polyacrylamide polymers and polyvinyl alcohol polymers. Examples of particularly preferred nonionic water-absorptive polymers include N-vinylcarboxylic amide polymers, inter alia, N-vinylacetamide.

N-vinylcarboxylic amide polymers are water-absorptive polymers that can be formed by polymerizing a compound of formula (I) typically in the presence of at least one crosslinking agent.

N-vinylcarboxylic amide polymers are water-absorptive polymers which find a wide range of utility, and are disclosed in Japanese Patent Application Laid-Open (kokai) Nos. 3-223304 and 4-323213 as being water-absorptive polymers which absorb not only water but also electrolytic solutions and aqueous liquids containing polyvalent metal ions with a swelling ratio higher than that exhibited by conventional water-absorptive polymers.

An N-vinylcarboxylic amide polymer is typically prepared by the following steps.

That is, an N-vinylcarboxylic amide polymer can be manufactured through polymerization of a monomer containing N-vinylcarboxylic amide (typically N-vinylacetamide; these compounds may be manufactured through a known method such as pyrolysis of N-(α-alkoxyalkyl)carboxylic amide described, for example, in Japanese Patent Application Laid-Open (kokai) No. 50-76015) represented by the above-described formula (I) typically with a crosslinking agent.

Examples of the crosslinking agent used in polymerization include a compound having two or more ethylenic unsaturated groups in one molecule, such as N,N'-methylenebis(acrylamide), ethylene glycol di(meth) acrylate, diethylene glycol di(meth)acrylate, triethylene glycol di(meth)acrylate, polyethylene glycol di(meth)acrylate, trimethylolpropane tri(meth)acrylate, pentaerythritol tri (meth)acrylate, divinylbenzene, divinyl ether, N,N'-butylenebis(N-vinylacetamide), N,N'-diacetyl-N,N'-divinyl-1,4-bisaminomethylcyclohexane, diethylene glycol diallyl ether, trimethylolpropane triallyl ether, tetraallyloxyethane, pentaerythritol triallyl ether, diallyl adipate, diallyl terephthalate, divinyl oxalate, divinyl succinate, divinyl malonate, divinyl adipate, divinyl maleate, trivinyl citrate, and tetravinyl pyromellitate.

These crosslinking agents may be used in the polymerization in an amount of 10/90–0.0001/99.9999 represented by a weight ratio of the crosslinking agent to a monomer, particularly preferably 2/98–0.0005/99.9995. When the amount of the cross-linking agent is excessive with respect to that of a starting monomer compound (in excess of 10/90 of the above-described ratio), an extremely high cross-linking density of the resultant N-vinylcarboxylic amide polymer is obtained to make the swelling ratio too small. In contrast, when the amount of a starting monomer compound is excessive with respect to that of the cross-linking agent (in excess of 0.0001/99.9999 of the above-described ratio), formation of a water-soluble or hydrophilic polymer which does not participate in the cross-linking reaction becomes predominant. Both cases are disadvantageous in that the resultant polymers substantially exhibit poor effects when serves as a water-absorptive polymer.

Alternatively, the N-vinylcarboxylic amide polymer may be manufactured through copolymerization of the above-described N-vinylcarboxylic amide with another copolymerizable ethylenic unsaturated compound in a certain amount so long as the water absorption or durability of the polymer does not decrease.

Examples of the ethylenic unsaturated compound include, but are not limited to, (meth)acrylic acid, a (meth)acrylic acid metal salt, methyl (meth)acrylate, ethyl (meth)acrylate, propyl (meth)acrylate, hydroxyethyl (meth)acrylate, hydroxypropyl (meth)acrylate, (meth)acrylamide, dimethylaminoethyl (meth)acrylate, a dimethylaminoethyl (meth) acrylate methyl chloride quaternary salt, N-dimethylaminopropyl(meth)acrylamide, an N-dimethylaminopropyl(meth)acrylamide methyl chloride quaternary salt, acrylonitrile, a 2-acrylamide-2-methylpropanesulufonic acid metal salt, vinyl acetate, vinyl compounds such as vinyl ethers and vinyl ketones, a vinylsulfonic acid metal salt, maleic acid, a maleic acid metal salt, fumaric acid, a fumaric acid metal salt, itaconic acid, and an itaconic acid metal salt.

In order to attain excellent properties of the above-described N-vinylcarboxylic amide polymer, these ethylenic unsaturated compounds should be incorporated in the starting compound in an amount of less than 50 wt. % (content of the above-described N-vinylcarboxylic amide; 50 wt. % or more), preferably less than 30 wt. %.

When the content of the ethylenic unsaturated compound is in excess of 50 wt. %, the resultant N-vinylcarboxylic amide polymer disadvantageously inhibits growth of plants and durability of the polymer decreases.

Polymerization is performed through a generally known method such as aqueous solution polymerization, reversephase suspension polymerization, reverse-phase emulsion polymerization, and precipitation-depositing polymerization.

The cross-linked N-vinylcarboxylic amide polymer exhibits two specific morphologic types; one is an N-vinylcarboxylic amide polymer having a high cross-linking density and a small grain size of the powder (hereinafter referred to as microgel-type N-vinylcarboxylic amide polymer) and the other is an N-vinylcarboxylic amide polymer having a comparatively high cross-linking density and a large grain size of the powder (hereinafter referred to as liquid-absorption-type N-vinylcarboxylic amide polymer).

These two types of the N-vinylcarboxylic amide polymer may be manufactured by appropriately selecting the above-described polymerization types.

That is, the former polymer, i.e., the microgel-type N-vinylcarboxylic amide polymer, is manufactured through the aforementioned precipitation-depositing polymerization (the organic solvent which does not dissolve the polymer is used for the polymerization: the monomers during the initial polymerization stage dissolve in the solvent, but the resultant polymer are deposited as fine grains because their solubility reduces as polymerization progresses). In contrast, the liquid-absorption-type N-vinylcarboxylic amide polymer is manufactured through either aqueous solution polymerization or reverse-phase suspension polymerization (water is normally used as the solvent for the polymerization, and water-containing hydrogel is obtained thereafter).

Customary radical polymerization catalysts are generally used as polymerization catalyst. There may be used, as a radical initiator, an azo initiator such as azobisisobutyronitrile, 2,2'-azobis (2-amidinopropane) dihydrocholoride, peroxide such as benzoylperoxide, and redox solvent (which permits peroxide or persulfate, and a reducing agent such as triethanolamine and sodium thiosulfate to exist in the same cycle) and the like.

Surface treatment such as surfactant treatment for improving the water absorbing rate and heat treatment for improving the gel strength may be performed on the thus obtained N-vinylcarboxylic amide polymer.

As described above, desired N-vinylcarboxylic amide polymers may be obtained.

There may be incorporated into the composition of the present invention, as an essential constituent component, commercially available N-vinylcarboxylic amide polymers as well as the thus-obtained N-vinylcarboxylic amide polymer. There are commercially available, as crosslinked insoluble N-vinylacetamide polymers, GX-205 (a microgel-type homopolymer of high density cross-linking comprised of N-vinylacetamide) and (a water absopitive, homopolymer of low density cross-linking comprised of N-vinylacetamide) and NA-300 (liquid-absorption-type N-vinylacetamide polymer) manufactured by Showa Denko K. K.. GE-191, a non-crosslinked soluble N-vinylacetamide polymer, manufactured by Showa Denko K.K. is also available.

Other nonionic water-absorptive polymers prepared in accordance with the known methods or other commercially available nonionic water-absorptive polymers may be used in the composition of the present invention.

B. The composition of the present invention comprises a "plant capable of growing in the presence of at least water and light" in combination with the aforementioned nonionic water-absorptive polymer such as N-vinylcarboxylic amide polymer as its essential component.

The expression "a plant capable of growing in the presence of at least water and light" refers to "an autotroph"

which is capable of performing photosynthesis under light irradiated thereto (sunlight in the case of the natural world), and thus does not require a supply of organic substances from the outside for its growth. In this sense, higher plants which require outside organic substances for their growth are excluded from the category of "plant capable of growing in the presence of at least water and light," even though they can perform photosynthesis.

Examples of the preferred plants capable of growing in the presence of at least water and light include, but are not limited to, plants which belong to algae, the Bryophyta and the Lichenes.

Algae which may be incorporated into the composition of the present invention are not particularly limited so long as they exhibit autotrophic characteristics, and freshwater algae and seawater algae may be used. Examples of the Algae include Chlorophyta such as Charoides (Charoides, *Lampro thamnium*, Nitellopsis, Nitella, etc.), Zynematales (Zygnema, Closterium, Netrium, etc.), Codials (*Codium frgile, Helimida opunta,* Caulerpa, etc.), *Bryopsis plumosa* (Bryopsis, Pseudobryopsis, Bryopsidella, Derbesis, Pedobesia, etc.), Acetabularia Ryukyuensis (Acetabularia Ryukyuensis, *Halicoryne wrightii, Neomeris annulata, Cymopolia van bossei, Bornettella ovalis, Acetabularia calyculus,* etc.), Siphonocladales (Valoniaceae, Boodleaceae, etc.), Cladophora (*Anadyomene writii,* Cladophora, *Cladophora sauteri,* Chaetomorpha, etc.), Ulva (Ulva, Fnteromorpha, etc.), Ulotrichales (Acrosiphoniaceae, Collinsiellaceae, Monostromaceae, Chlorocystidaceae, etc.), Prasiola, Chlorella, Chlorococcales (Pediastrum, Hydrodictyon, etc.), Volvocales (Chlamydomonus, Pandorina, Pleodorina, Volvox, etc.); Phodophyta such as *Ceramium kondoi* (Ceramiaceae, Delesseriaceae, Dasyaceae, Rhodomelaceae, etc.), *Rhodymenia intrincata* (Champiaceae, *Rhodymenia intricata,* etc.), *Gigartina terella* (Furcellariaceae, Nemastomaceae, Phyllophoraceae, Gracilariaceae, etc.), Cryptonemiaceae (Cryptonemnia, etc.), *Rhodymenia palamata,* Gelidiaceae (*Gelidiella acerosa,* etc.), *Bonnemaisonia hamifera* (Naccariaceae, *Nemalion vermiculare* (*Nemalion vermiculare,* Liagora, *Dermoneama frappieri,* Chaetangiaceae, etc.), Compsopogonaceae, *Bangia fusco-purpuria* (Bangia, Porphira, etc.), Porphyridiaceae (Porphyridium, Cyanidium, etc.); Phaeophyta such as, *Sargassum fulvellum* (Sargassuceae, *Cystophylillum hakodatense,* Dictyotaceae, etc.), Laminaria (Pseudochordariaceae, Chordariaceae, Laminariaceae, Alariaceae, Lessonia, etc.); Cyanophyta (Microcystis, Anabaena, Oscillatoria, Spirulina, *Aphanothece sacrum,* etc.); Glaucophyceae (Cyanophora, Glaucocysis, etc.); Cryptophyceae (Cryptomonas, Rhodomonas, etc.); Dinophyceae (Prorocentrum, Ornitbocercus, Peridinium, Gonyaulax, Ceratium, Gymnodinium, *Noctiluca scintillans,* Pyrocystis, etc.); Chrysophyceae (Ochromonas, Synura, Mallomonas, Dinobryon, etc.); Pacillariophyceae (Nannochloropsis, etc.); Xanthophyceae (Botrydium, Vaucheria, etc.); Haptophyceae (Emiliania, Pleurochrysis, etc.); Raphidophyceae (Chattonella, Heterosigma, etc.); Euglenophyceae; Chlorarachnion; Prochlorphyceae; Prasinophyceae; etc.

The Bryophyta which may be incorporated into the composition of the present invention are mosses (musci), liverworts (hepaticae), and hornworts (anthocerotae).

Examples of mosses (musci) include those which belong to the Rhacomitrium Brid. such as *Rhacomitrium canescens* (Hedw.) Brid., var. ericoides (Brid.) B.S.G., *Rhacomitrium lanuginosum* (Hedw.) Brid., *Rhacomitrium heterostichum* Hedw.) Brid., var. diminutum (Card.) Nog., *Rhacomitriun sudeticum* (Funck) B.S.G., *Rhacomitrium fasciculare* (Hedw.) Brid., *Rhacomitriun anomodontoides* Card., *Rhacomitrium carinatun* Card., and *Rhacomitrium aciculare* (Hedw.) Brid.; the Dicranum Hedw. such as *Dicranum scoparium* Hedw., *Dicranum japonicum* Mitt., *Dicranum nipponense* Besch., *Dicranum fuscescens* Turn., *Dicranum majus* Turn., *Dicranum caesium* Mitt., *Dicranum polysetum* Sw., *Dicranum elatum* Lindb., *Dicranum flagellare* Hedw., *D. mayrii* Broth., *Dicranum viride* (Sull. et Lesq.) Lindb. var. hakkodense (Besch.) Tak., *D. fulvum* Hook., *Dicranum hamulosum* Mitt., and *D. leiodontum* Card.; the Hypnum Hedw. such as *Hypnum plumaeforme* Wils., *Hypnum sakuraii* (Sak.) Ando, *Hypnum oldhamii* (Mitt.) Jaeg., *Hypnum calcicolum* Ando, *Hypnum fujiyamae* (Broth.) Paris, *Hypnum cupressiforme* Hedw., *Hypnum tristo-viride* (Broth.) Paris, *Hypnum pallescens* (Hedw.) P. Beauv., *Hypnum reptile* Michx., *Hypnum plicatulum* (Lindb.) Jaeg., *Hypnum subimponens* Lesq., *Hypnum erectius culum* Sull. et Lesq., and *Hypnum lindbergii* Mitt.; the Thuidium B.S.G. such as *Thuidium kanedae* Sak., *Thuidium cymbifolium* (Doz. et Molk.) Doz. et Molk., *Thuidium tamariscinum* (Hedw.) B.S.G., *Thuidium delicatulum* (Hedw.) Mitt., *T.recognitum* (Hedw.) Lindb., *Thuidium glaucinum* (Mitt.) Bosch et Lac., and *Thuidium bipinnatulum* Mitt.; the Climacium Web. et Mohr such as *Climacium japonicum* Lindb., and *Climacium dendroides* (Hedw.) Web. et Mohr; the Rhizogonium Brid. such as *Rhizogonium dozyanum* Lac., *Rhizogonium badakense* Fl., and *R. spiniforme* (Hedw.) Brunch.

Examples of liverworts (hepaticae) include those which belong to the Heteroscyphus Schiffn. such as *Heteroscyphus planus* (Mitt.) Schiffn., *Heteroscyphus argutus* (Reinw. et al.) Schiffn., *Heteroscyphus bescherellei* (Steph.) Hatt., *Heteroscyphus lophocoleoides* Hatt., *Heteroscyphus tener* (Steph.) Schiffn., and *Heteroscyphus javanicus* (Steph.) Schiffn.; the Bazzania S. Gray such as *Bazzania japonica* (Lac.) Lindb., *Bazzania yoshinaga* (Steph.) Steph., *Bazzania fauriana* (Steph.) Hatt., *Bazzania trilobata* (L.) S. Gray, *Bazzania ambigua* (Lindenb.) Trev. subsp. ovifolia (Steph.) Hatt., *Bazzania bidentula* (Steph.) Steph., *Bazzania tricrenata* (Wahl.) Lindb., *Bazzania pearsonii* Steph., *Bazzania pompeana* (Lac.) Mitt., *Bazzania tridens* (Reinw. et al.) Trev., and *Bazzania mayebarae* Hatt.; the Porella L. such as *Porella perrottetiana* (Mont.) Trev., *Porella stephaniana* (Mass.) Hatt., *Porella campylophylla* (Lehm. et Lindenb.) Trev. subsp. tosana (Steph.) Hatt., *Porella caespitans* (Steph.) Hatt. var. setigera (Steph.) Hatt., *Porella japonica* (Lac.) Mitt., *Porella oblongifolia* Hatt., *Porella grandiloba* Lindb., *Porella vernicosa* Lindb., *Porella fauriei* (Steph.) Hatt., and *Porella gracillima* Mitt..

The composition of the present invention may comprises hornworts (anthocerotae) such as Phaeoceros Prosk., Anthoceros L., Megaceros Campb., Dendroceros Nees, and Notothylas Sull.

Also, the Lichenes that may be incorporated into the composition of the present invention are not particularly limited, so long as they have the aforementioned autotrophic characteristics. There may be employed any members which belong to the ascolichenes, basidiolichenes, and deuterolichenes.

Also, the aforementioned plants capable of growing in the presence of at least water and light may be those which are in the stage in which their autotropic characteristics are exhibited, or in other words, their photosynthesis ability is exhibited. Moreover, there may be used, as a constituent component of the present invention, plants which are in the stage in which their photosynthesis ability has not yet been acquired in the course of their growth.

For example, there may be incorporated, as a constituent component of the present invention; among the aforementioned algae, mainly the sporophyte or the gametophyte, or the spore; among the Bryophyta, mainly the plant body, or the spore; and among the Lichenes, mainly thallus.

The aforementioned plants may be incorporated into the composition of the present invention singly or in combination of two or more.

As water, which is an essential constituent component of the present invention, seawater may be used.

C. A composition of the invention comprises a nonionic water-absorptive polymer, such as the aforementioned N-vinylcarboxylic amide polymer, containing at least water, and any of the aforementioned plants mixed in as an essential element.

Upon contact with water, a nonionic water-absorptive polymer, such as the aforementioned N-vinylcarboxylic amide polymer, absorbs water and swells to become a water-containing product, i.e. a so-called hydrogel. A composition of the invention assumes the gross form of a number of hydrogel bodies, or hydrogel aggregate, thereby yielding desired effects.

The state of the hydrogel aggregate can be freely changed somewhere between an apparently fluid state and an apparently nonfluid state by appropriately selecting the grain size of the aforementioned N-vinylcarboxylic amide polymer, degree of cross-linking, the amount of water to be brought into contact with the polymer, the total amount of hydrogel bodies to be used, and the like. Generally, a hydrogel aggregate is considered fluid when its kinetic viscosity is less than 500 stokes as measured at ambient temperature by Gardner's bubble viscometer, and is considered nonfluid when its kinetic viscosity is not less than 500 stokes as measured in the same manner.

Since there are many determinant factors of the fluidity of a hydrogel aggregate as mentioned above, it is difficult to unitarily determine the fluidity of a hydrogel aggregate through adjustment of the factors. However, the fluidity of a hydrogel aggregate can be generally determined with reference to a commercially available nonionic water-absorptive polymer such as the aforementioned N-vinylcarboxylic amide polymer, since such polymers allow substantially uniform adjustment of the factors.

In the case of an N-vinylcarboxylic amide polymer, an apparently fluid hydrogel aggregate having a kinetic viscosity of less than 500 stokes at ambient temperature can be manufactured by, for example, (1) bringing 1 g of NA-010 having an average grain size of not greater than 50 $\mu$m into contact with at least 40 g of water or (2) bringing 1 g of GX-205 having an average grain size of not greater than 1 $\mu$m into contact with at least 30 g of water. Further, an apparently fluid hydrogel aggregate can be manufactured by bringing 1 g of GE-191 into contact with at least 50 g of water.

An apparently nonfluid hydrogel aggregate having a kinetic viscosity of not less than 500 stokes at ambient temperature can be manufactured by, for example, (1) bringing 1.0 g of NA-010 having an average grain size of 100–1000 $\mu$m into contact with 10–30 g of water or (2) bringing 1 g of GX-205 having an average grain size of not greater than 1 $\mu$m into contact with 5–9 g of water.

In examples described later, a low-viscosity composition of the invention refers to a composition of the invention having a kinetic viscosity of less than 500 stokes at ambient temperature. By contrast, a high-viscosity composition of the invention refers to a composition of the invention having a kinetic viscosity of not less than 500 stokes at ambient temperature.

As described above, among nonionic water-absorptive polymers, an N-vinylcarboxylic amide polymer efficiently absorbs not only water but also alcohol, brine, and the like. Accordingly, elements other than water can be also incorporated into a composition of the present invention in accordance with the cultivation environment for the aforementioned plants.

However, incorporating an organic substance into a composition of the invention causes to the composition contamination with various germs, thus impairing the important feature of the invention "noncontamination with various germs."

Accordingly, elements other than water that can be contained in a composition of the invention are practically inorganic substances. For example, sodium chloride, calcium chloride, or the like can be added to a composition of the invention.

D. A combination of components of a composition of the invention may be selected in accordance with a plant to be incorporated into and the use for the composition. Examples of such a combination are described below.

(1) A plant growing with fresh water, such as Bryophyta, Lichenes, or freshwater algae, is contained in a composition of the invention:

In this case, for a plant to be contained in a composition of the invention, a composition of the invention does not need to contain additional elements other than water, so long as an environment providing light is established.

Accordingly, a composition of the invention is preferably a "composition consisting of a plant capable of growing in the presence of at least water and light, a nonionic water-absorptive polymer such as an N-vinylcarboxylic amide polymer, and water."

(2) An oceanic plant, such as algae growing in the sea, is contained in a composition of the invention:

In this case, for a plant to be contained in a composition of the invention, a composition of the invention preferably establishes an environment similar to seawater. Also, an N-vinylcarboxylic amide polymer must be selected for use as a nonionic water-absorptive polymer.

Accordingly, a composition of the invention is preferably a "composition comprising a plant capable of growing in the presence of at least water and light, an N-vinylcarboxylic amide polymer, and water," i.e. a composition containing "inorganic substances contained in seawater, such as sodium chloride, as well as water." Also, seawater may be brought into contact with an N-vinylcarboxylic amide polymer to obtain a composition of the invention.

(3) As described above, a nonionic water-absorptive polymer to be used, such as an N-vinylcarboxylic amide polymer, the amount of water to come into contact with the polymer, and like factors may be selected in accordance with a desired property of a composition of the invention (i.e. whether its kinetic viscosity is not less than or less than 500 stokes at ambient temperature).

Surprisingly, in the thus-prepared composition of the invention, a plant incorporated into the composition continues growing only by placing the composition under sunshine and/or temperature conditions suited for growth of the plant.

That is, a composition of the present invention, or a composition comprising a nonionic water-absorptive polymer, such as an N-vinylcarboxylic amide polymer, and water can serve as a cultivation carrier for a "plant capable of growing in the presence of at least water and light."

The inventors of the present invention propose not only a composition of the invention but also the employment of a nonionic water-absorptive polymer, particularly an N-vinylcarboxylic amide polymer, more particularly an N-vinylacetamide polymer, as a cultivation carrier for a plant.

E. A composition of the invention is applicable to various fields as exemplified below.

(1) A composition of the invention can be used as the basic portion of an "environment-cleaning reactor," which converts carbon dioxide contained in the atmosphere to oxygen and emits oxygen and in addition trace substances emitted by plants.

In this case, among the aforementioned plants, a plant having a good photosynthetic efficiency, for example, chlorella, is preferably used.

In contrast with a conventional system which employs a large-scale apparatus for effecting circulation within the system, the "environment-cleaning reactor" has an advantageous feature that such a large-scale apparatus is not necessarily required.

(2) A composition of the invention has potential appeal to one's aesthetic sense.

That is, a composition containing a nonionic water-absorptive polymer, such as an N-vinylacetamide polymer, and water is basically transparent, so that a user can directly enjoy the color of a plant incorporated into the composition.

For example, through use of a composition of the invention as an element of building material, a plant mixed in the composition serves as an ornamental object and effects an environmental-cleaning action.

(3) A composition of the invention can be used as means for artificially cultivating the aforementioned plants.

Conventionally, the artificial cultivation of any of the aforementioned plants requires the employment of a large-scale jar fermenter or like apparatus equipped with a stirrer in order to feed oxygen to the plant and to prevent the plant from adhering to the apparatus. By contrast, through employment of a composition of the invention, the aforementioned plants can be cultivated without use of such a large-scale cultivation apparatus.

(4) A composition of the invention can serve as means for studying the ecology of the aforementioned plants.

The life environment of many of the aforementioned plants is not sufficiently known. A composition of the invention may serve as excellent means for elucidating such a life environment through growing the plants in the composition.

(5) Through use of a composition of the invention containing Bryophyta, a nonionic water-absorptive polymer, and water, there can be easily and efficiently manufactured revegetation materials, which will be described later in detail.

Conventionally, Bryophyta, or mosses have a negative reputation like "damp" or "dark," and their applications are limited to gardens, bonsai, and like fields.

However, various kinds of mosses have not only a unique reposing tone of color as represented by the word "moss green" and as observed in no other plants, but also the astonishing characteristic "even after moss is separated and dried, watering revives its life activity," a phenomenon observed with no other higher plants.

Regretfully, the excellent characteristics of mosses are not sufficiently utilized in industrial fields.

As a result of intensive attempts to apply mosses having such excellent characteristics to various fields where environmental revegetation is needed, the present inventors have selected revegetation substrates that use moss (refer to Japanese Patent Application Laid-Open (kokai) Nos. 7-227142 and 7-227143). However, the revegetation substrates require moss to be secured through use of fixation means, specifically through sewing, and thus are not necessarily satisfactory in terms of cost.

The present inventors have found that, through use of a composition of the present invention containing Bryophyta, a nonionic water-absorptive polymer, and water, moss can be secured more simply and efficiently than in the case of conventional revegetation substrates where moss is secured through use of fixation means; consequently, revegetation materials such as revegetation substrates can be manufactured simply and efficiently.

The present inventors have created a certain revegetation material in which moss bodies intertwine in a desired shape. Specifically, moss bodies are brought into contact with a certain nonionic water-absorptive polymer, such as an N-vinylcarboxylic amide polymer, swollen with water, to obtain a composition. The thus-obtained composition is filled into a closed system having a desired shape and ventilation means so as to cultivate the moss within the system. As a result, moss bodies in contact with the polymer intertwine to form the revegetation material.

The revegetation material is manufactured in the following manner.

A composition containing Bryophyta, a nonionic water-absorptive polymer, and water is placed in a container formed of a waterproof material and having ventilation means so as to cultivate the plant contained in the composition. Through cultivation, moss bodies intertwine within the cultivation system. Subsequently, the nonionic water-absorptive polymer is removed from the cultivation system.

Specifically, the method of manufacturing the revegetation material includes:

1. a first step of dispersing moss bodies in a system composed of a hydrogel aggregate prepared by swelling a nonionic water-absorptive polymer with water, placing the thus-formed dispersion into a container formed of a waterproof material having ventilation means so as to form a moss cultivation system within the container, and closing the container;

2. a second step of cultivating the moss bodies in the moss cultivation system manufactured in the first step so that the moss bodies intertwine; and 3. a third step of removing the moss cultivation system from the container and removing the nonionic water-absorptive polymer from the moss cultivation system.

The "revegetation material" refers to a material used to revegetate a desired portion in the environment where moss can grow. The shape of the "revegetation material" is not particularly limited. Also, the "revegetation substrate" refers to a revegetation material having the shape of a substrate.

Among nonionic water-absorptive polymers, an N-vinylcarboxylic amide polymer efficiently absorbs not only water but also alcohol, brine, and the like. Accordingly, elements can be used in addition to water in accordance with cultivation environment for the aforementioned moss.

However, using an organic substance causes contamination to the gel aggregate with various germs. Accordingly, elements other than water that can be incorporated into the gel aggregate are practically inorganic substances. For example, sodium chloride, calcium chloride, or the like can be used in addition to water.

In the first step, the aforementioned gel aggregate is placed in the container formed of a waterproof material and having ventilation means to thereby bring the gel aggregate into contact with moss (described later).

In dispersion, after the gel aggregate is filled into the container, the moss may be dispersed in the gel aggregate. Alternatively, the gel aggregate and the moss may be mixed to thereby disperse the moss in the gel aggregate system, and then the thus-mixed composition may be filled into the container.

The method of preparing the moss cultivation system is not particularly limited so long as moss bodies are finally dispersed in the system composed of a hydrogel aggregate of a nonionic water-absorptive polymer contained in the container formed of a waterproof material and having ventilation means.

The waterproof material for the manufacture of the container is not particularly limited. Examples of the waterproof material include waterproof plastics, metal, glass, and ceramics. Among these materials, plastics are particularly preferred in view of their advantages of low cost, durability, and easy observation of the growing state of moss.

Also, ventilation means is not particularly limited. For example, after a container is filled with moss and a gel aggregate, holes may be formed in the container wall. Further, a silicone resin having both waterproofing and ventilating functions may be used as the waterproof material. In the manufacture of a revegetation material, ventilation means may not be provided. However, if ventilation means is not provided, the growth of moss becomes very slow; consequently, the production efficiency of revegetation materials is impaired.

The shape of the container may be selected as appropriate in accordance with a desired shape of a revegetation material. For example, when a revegetation material is to assume the form of a revegetation substrate, the container may have the shape of a flat plate.

The first step may be performed in the above-describe manner so as to form a desired moss cultivation system.

In the second step, the moss is cultivated in the moss cultivation system manufactured in the first step so that moss bodies in the system intertwine.

In the second step, the moss cultivation system, which is prepared in the first step and contains the gel aggregate serving as a cultivation carrier for the contained moss, is allowed to stand under sunshine and/or temperature conditions suited for growth of the moss. As a result, surprisingly, moss bodies dispersed in the moss cultivation system grow and intertwine to assume the basic form of a desired revegetation material.

The above-mentioned "sunshine and/or temperature conditions suited for growth of the moss" generally refers to a shady condition. Even when a selected moss is a moss which essentially prefers sunshine (described later), the moss cultivation system is preferably allowed to stand in the shade. If the cultivation system is directly exposed to sunshine, the temperature of the cultivation system rises excessively, so that the growth of the moss rather tends to be hindered. The cultivation system, when exposed to sunshine, is preferably exposed to sunshine to such a degree that its temperature does not rise. When a moss which essentially prefers shade (described later) is selected, the cultivation system must be more strictly left in the shade.

The second step may be performed in the above-described manner so as to yield the basic form of a revegetation material.

In the third step, the basic form of a revegetation material is removed from the container, and the nonionic water-absorptive polymer is removed from the basic form of a revegetation material.

This removal can be effected merely by washing off the nonionic water-absorptive polymer in water.

The washed-off nonionic water-absorptive polymer can be used again in the manufacture of a revegetation material.

A revegetation material is manufactured in the above-described manner. A regenerative material can be used either in the wetted state or in the dried state, but is preferably used in the dried state in view of actual transport and ease of handling. The method of drying a revegetation material is not particularly limited. A revegetation material may be dried naturally in the sunlight or dried artificially by a drying machine which is set to moderate drying conditions so as not to weaken the moss.

A revegetation material may be emplaced in any site so long as the environmental conditions of the site are suited for growth of moss. Examples of such an installation site include parks and faces of slopes of roads and river banks. of course, a site must be selected in accordance with sunshine conditions required for growth of a selected moss. For example, when a moss which prefers relatively strong sunshine, such as *Rhacomitrium canescens* (Hedw.) Brid., is selected, the revegetation material is preferably emplaced in a relatively sunny site. When a moss which prefers shade, such as *Thuidium kanedae,* is selected, the revegetation material is preferably emplaced in the shade to the extent possible.

When water is sprinkled over an emplaced revegetation material for about one month, the moss newly germinates, and, after that, its cultivation in natural precipitation is enabled. Thus, the site can be revegetated with the moss.

The present invention will next be described by way of example, which should not be construed as limiting the invention.

EXAMPLE 1

Manufacture of a High-Viscosity Composition of the Invention Containing Fine Algae Fine algae (a mixture of various kinds of fine algae) were used as a plant element to be contained in a high-viscosity composition of the invention to be manufactured in the present example.

40 ml of water (city water; the same is applied to Examples and Test Examples appearing below) were brought into contact with 1.7 g of NA-010 (trade name of a liquid-absorptive N-vinylacetamide polymer manufactured by Showa Denko K. K.) to obtain a high-viscosity hydrogel aggregate. 10 ml of an aqueous suspension of the fine algae were mixed into the obtained hydrogel aggregate to obtain a desired high-viscosity composition of the invention.

The thus-obtained high-viscosity composition of the invention containing fine algae was filled into an airtight bag having packing (trade name: UNIPACK; manufactured by Seinichi Co., Ltd.) to obtain a composition A of the invention. The composition A was subjected to the cultivation test of Test Example 1, which will be described later.

EXAMPLE 2

Manufacture of aHigh-Viscosity Composition of the Invention Containing Moss Spores Spores derived from five sporophytes of *Rhodobryum giganteum* (Schwaegr.) Par. were used as a plant element to be contained in a high-viscosity composition of the invention to be manufactured in the present example.

40 ml of water were brought into contact with 1.7 g of NA-010 (trade name of a product manufactured by Showa Denko K.K.) to obtain a high-viscosity hydrogel aggregate. 10 ml of an aqueous suspension of the above spores of *Rhodobryum giganteum* (Schwaegr.) Par. were mixed into the obtained hydrogel aggregate to obtain a desired high-viscosity composition of the invention.

The thus-obtained high-viscosity composition of the invention containing the spores of *Rhodobryum giganteum* (Schwaegr.) Par. was filled into an airtight bag having packing (trade name: UNIPACK; manufactured by Seinichi Co., Ltd.) to obtain a composition B of the invention. The composition B was subjected to the cultivation test of Test Example 1, which will be described later.

Example 3
Manufacture of a High-Viscosity Composition of the Invention Containing Moss Bodies Cultivated *Rhacomitrium canescens* (Hew.) Brid. were cut at a portion located 3–8 mm from its top caulis to obtain fragments of its plant bodies. The fragments of plant bodies of *Rhacomitrium canescens* (Hew.) Brid. were well washed in water and were used as a plant element to be contained in a high-viscosity composition of the invention to be manufactured in the present example.

40 ml of water were brought into contact with 1.7 g of NA-010 (trade name of a product manufactured by Showa Denko K.K.) to obtain a high-viscosity hydrogel aggregate. 32 g of the above fragments of plant bodies of *Rhacomitrium canescens* (Hew.) Brid. were mixed into the obtained hydrogel aggregate to obtain a desired high-viscosity composition of the invention.

The thus-obtained high-viscosity composition of the invention containing fragments of plant bodies of *Rhacomitrium canescens* (Hew.) Brid. was filled into an airtight bag having packing (trade name: UNIPACK; manufactured by Seinichi Co., Ltd.) to obtain a composition C of the invention. The composition C was subjected the cultivation test in Test Example 1, which will be described later.

EXAMPLE 4
Manufacture of a High-Viscosity Composition of the Invention Containing Oceanic Algae (seaweed)

Seawater was sampled from the sea off the coast of Akita Prefecture in winter. Green laver living in the sampled seawater was used as a plant element to be contained in a high-viscosity composition of the invention to be manufactured in the present example.

30 ml of the sampled seawater were brought in contact and mixed with 0.5 g of NA-010 (trade name of a product manufactured by Showa Denko K.K.) to obtain a desired high-viscosity composition of the invention.

The thus-obtained high-viscosity composition of the invention containing green laver was filled into an airtight bag having packing (trade name: UNIPACK; manufactured by Seinichi Co., Ltd.) to obtain a composition D of the invention. The composition D was subjected the cultivation test in Test Example 1, which will be described later.

Example 5
Manufacture of a Low-Viscosity Composition of the Invention Containing Fine Algae The fine algae used in Example 1 were used as a plant element to be contained in a low-viscosity composition of the invention to be manufactured in the present example. 16 ml of water were brought into contact with 0.2 g of GX-205 (trade name of a microgel type N-vinylacetamide polymer manufactured by Showa Denko K.K.) to obtain a low-viscosity hydrogel. 4 ml of an aqueous suspension of the fine algae were mixed into the obtained hydrogel to obtain a desired low-viscosity composition of the invention.

The thus-obtained low-viscosity composition of the invention containing the fine algae was placed into a test tube to obtain a composition E of the invention. The composition E was subjected the cultivation test in Test Example 2, which will be described later.

EXAMPLE 6
Manufacture of a Low-Viscosity Composition of the Invention Containing Spores of Moss The protonema of *Rhodobryum giganteum* (Schwaegr.) Par. was used as a plant element to be contained in a low-viscosity composition of the invention to be manufactured in the present example.

25 ml of water were brought into contact with 0.2 g of GX-205 (trade name of a microgel type N-vinylacetamide polymer manufactured by Showa Denko K.K.) to obtain a low-viscosity hydrogel. 4 ml of a suspension of the protonema of *Rhodobryum giganteum* (Schwaegr.) Par. corresponding to 5 sporophytes of *Rhodobryum giganteum* (Schwaegr.) Par. in 10 ml of water were mixed into the obtained hydrogel to obtain a desired low-viscosity composition of the invention.

The thus-obtained low-viscosity composition of the invention containing the spores of *Rhodobryum giganteum* (Schwaegr.) Par. was placed into a test tube to obtain a composition F of the invention. The composition F was subjected the cultivation test in Test Example 2, which will be described later.

EXAMPLE 7
Manufacture of a Low-Viscosity Composition of the Invention Containing Moss Bodies As in the case of Example 3, fragments of plant bodies of *Rhacomitrium canescens* (Hew.) Brid. were used as a plant element to be contained in a low-viscosity composition of the invention to be manufactured in the present example.

16 ml of water were brought into contact with 0.2 g of GX-205 (trade name of a microgel type N-vinylacetamide polymer manufactured by Showa Denko K.K.) to obtain a low-viscosity hydrogel. 6 g of the above fragments of plant bodies of *Rhacomitrium canescens* (Hew.) Brid. were mixed into the obtained hydrogel as in the case of Example 3, to obtain a desired low-viscosity composition of the invention.

The thus-obtained low-viscosity composition of the invention containing the fragments of plant bodies of *Rhacomitrium canescens* (Hew.) Brid. was placed into a test tube to obtain a composition G of the invention. The composition G was subjected the cultivation test in Test Example 2, which will be described later.

TEST EXAMPLE 1
Plant Cultivation Test of the High-Viscosity Compositions of the High-Viscosity Compositions of the Invention The packed high-viscosity compositions A to D manufactured in Examples 1–4 were hung on the wall of an ordinary room and allowed to stand intact for one year.

(1) Composition A of the Invention

When manufactured, the composition A was of a hardly recognizably light green color. However, one year after the manufacture, even though there was observed a slight reduction in the amount of water in the packed hydrogel, the fine algae contained in the hydrogel were far from becoming weak, but increased in amount to assume a darker green color than at the beginning of the test.

As a result of microscopic observation of the fine algae contained in the composition A conducted at the beginning of the test and one year later, sufficient chloroplasts were observed without recognizable anomaly even after one year.

Figure 1:
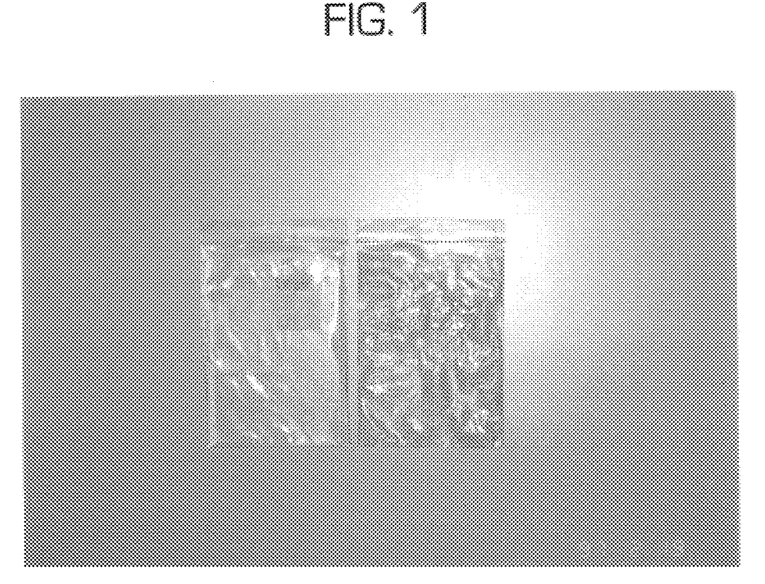
FIG. 1 is a morphological photo comparing the composition A (left) equivalent to that observed immediately after the start of a plant cultivation test and the composition A (right) observed one year later.

FIG. 1: A morphological photo comparing the composition A (left) equivalent to that observed immediately after the start of the test and the composition A (right) observed one year later. The left-hand composition A was manufactured at the end of the test under conditions identical to those at the beginning of the test.

Figure 2:
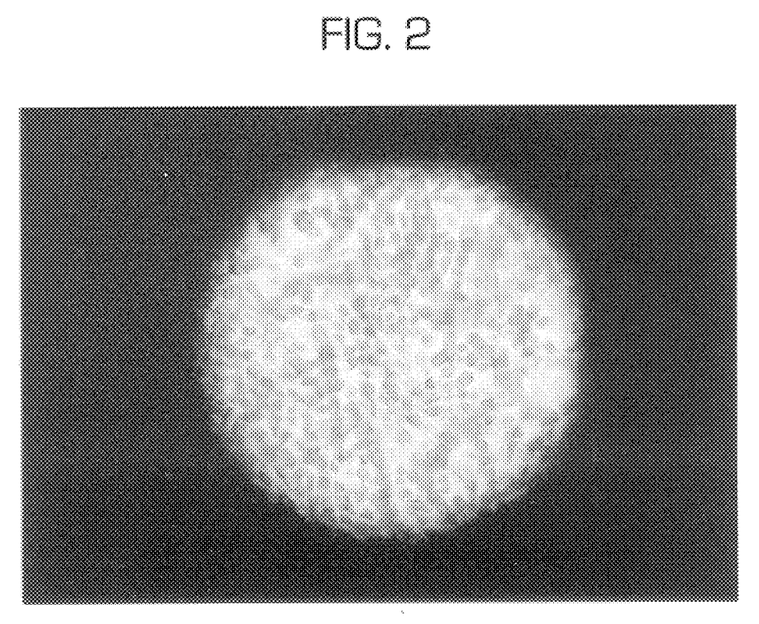
FIG. 2 is a micrograph (×400) showing the morphology of fine algae as observed at the beginning of the test.

FIG. 2: A micrograph (×400) showing the morphology of the fine algae as observed at the beginning of the test.

Figure 3:
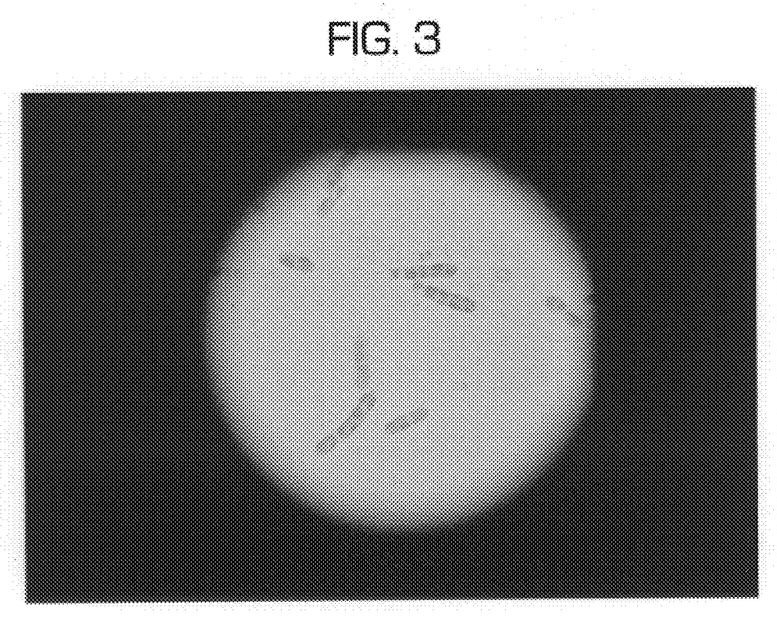
FIG. 3 is a micrograph (×400) showing the morphology of fine algae as observed at the end of the test.

FIG. 3: A micrograph (×400) showing the morphology of the fine algae as observed at the end of the test. The fine algae of this photo show no morphological difference from those in FIG. 2.

(2) Composition B of the Invention

When manufactured, the composition B was of a hardly recognizably light green color. However, one year after the manufacture, even though there was observed a slight reduction in the amount of water in the packed hydrogel, the spores of *Rhodobryum giganteum* (Schwaegr.) Par. contained in the hydrogel were far from becoming weak, but assumed a darker green color than at the beginning of the test.

As a result of the time-course microscopic observation of the spores of *Rhodobryum giganteum* (Schwaegr.) Par. contained in the composition B, surprisingly, germination of the spores was observed.

As a result of microscopic observation of the *Rhodobryum giganteum* (Schwaegr.) Par. conducted at the beginning of the test and one year later, sufficient chloroplasts were observed without recognizable anomaly even after one year.

Figure 4:
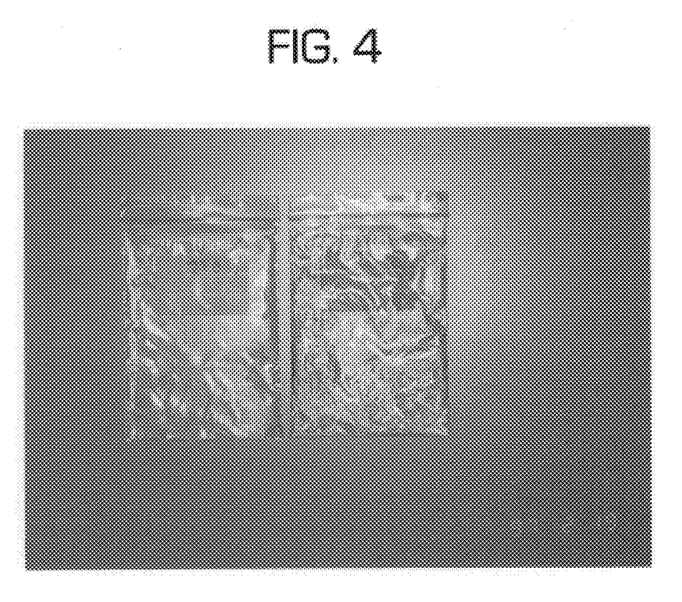
FIG. 4 is a morphological photo comparing the composition B (left) equivalent to that observed immediately after the start of a plant cultivation test and the composition B (right) observed one year later.
Figure 5:
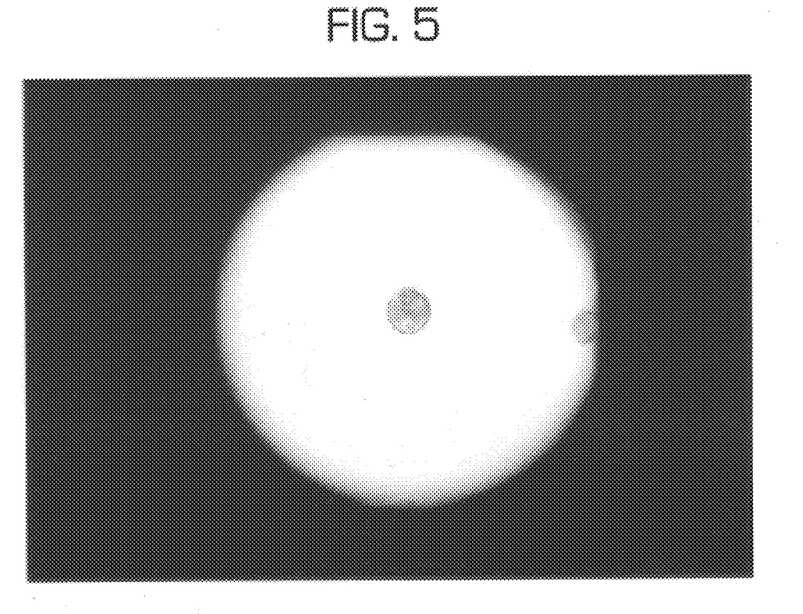
FIGS. 5–10 are time-course morphological photos showing the growth of the spores of *Rhodobryum giganteum* (Schwaegr.) Par., ranging from the morphology (FIG. 5) observed at the beginning of the test to the morphology (FIG. 10) observed at the end of the test.
Figure 6:
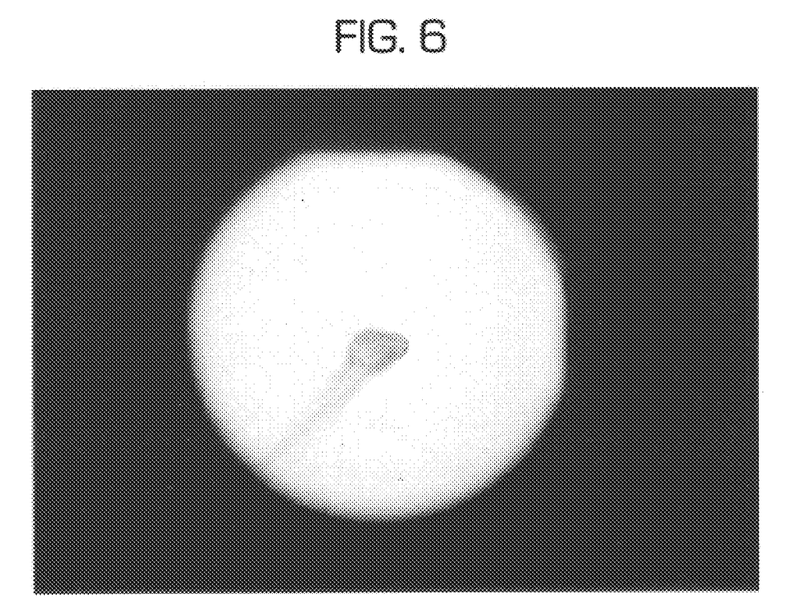
Figure 7:
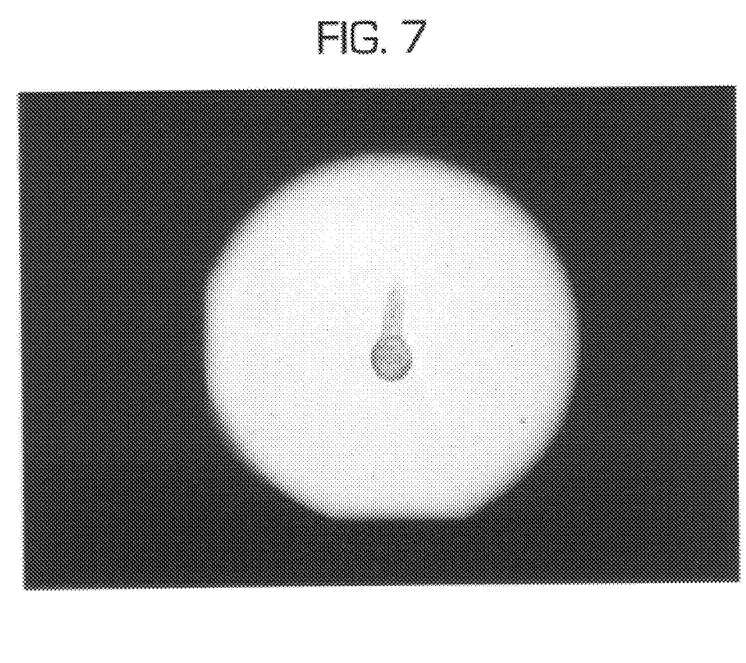
Figure 8:
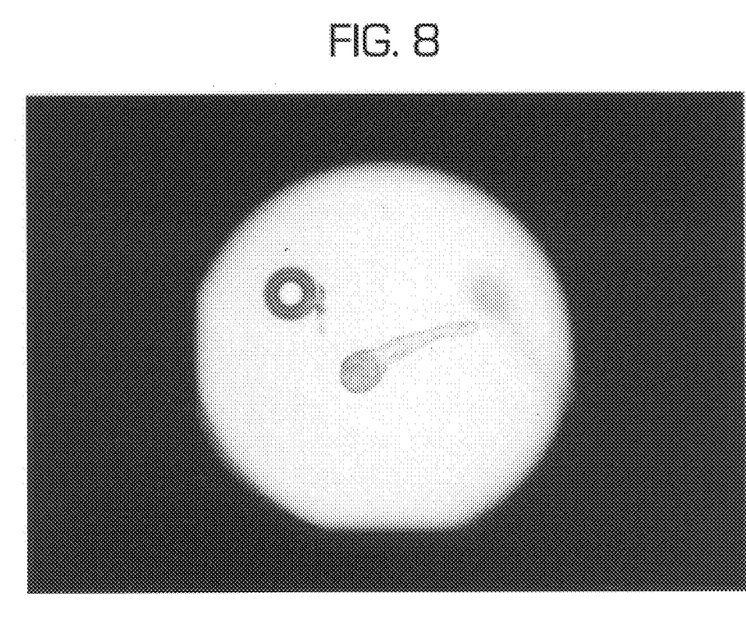
Figure 9:
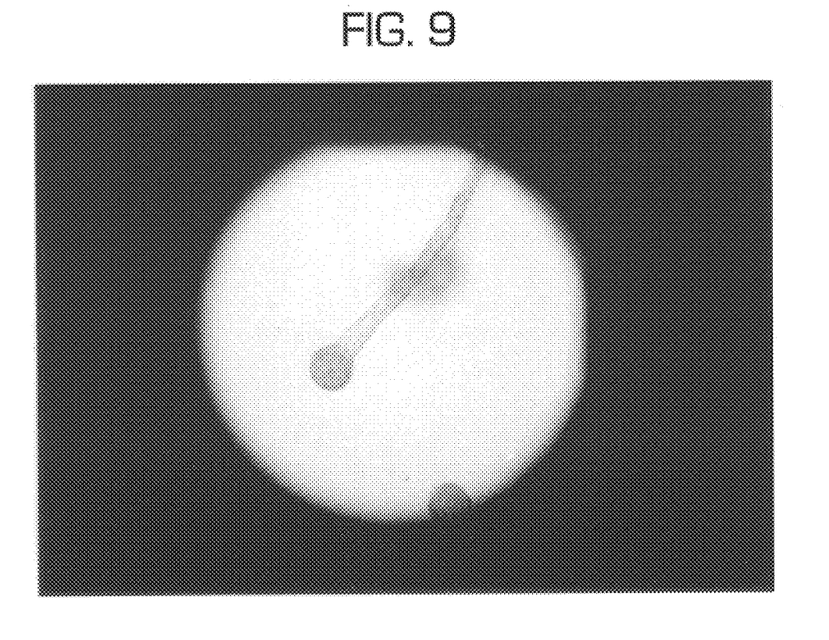
Figure 10:
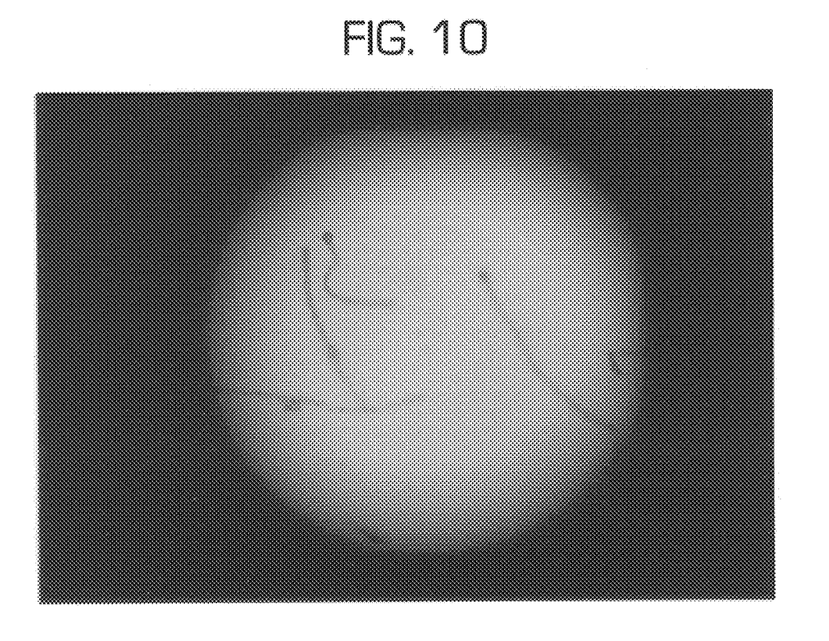

FIG. 4: A morphological photo comparing the composition B (left) equivalent to that observed immediately after the start of the test and the composition B (right) observed one year later. The left-hand composition B was manufactured at the end of the test under conditions identical to those at the beginning of the test.

FIGS. 5–10: Time-course morphological photos showing the growth of the spores of *Rhodobryum giganteum* (Schwaegr.) Par., ranging from the morphology (FIG. 5) observed at the beginning of the test to the morphology (FIG. 10) observed at the end of the test. These photos show that the spores of *Rhodobryum giganteum* (Schwaegr.) Par. germinate favorably.

(3) Composition C of the Invention

One year after manufacture, even though the composition C showed a slight reduction in the amount of water contained in the gel, the fragments of plant bodies of *Rhacomitrium canescens* (Hew.) Brid. contained in the composition C were far from becoming weak, and all of the fragments grew from the time of manufacture.

Figure 11:
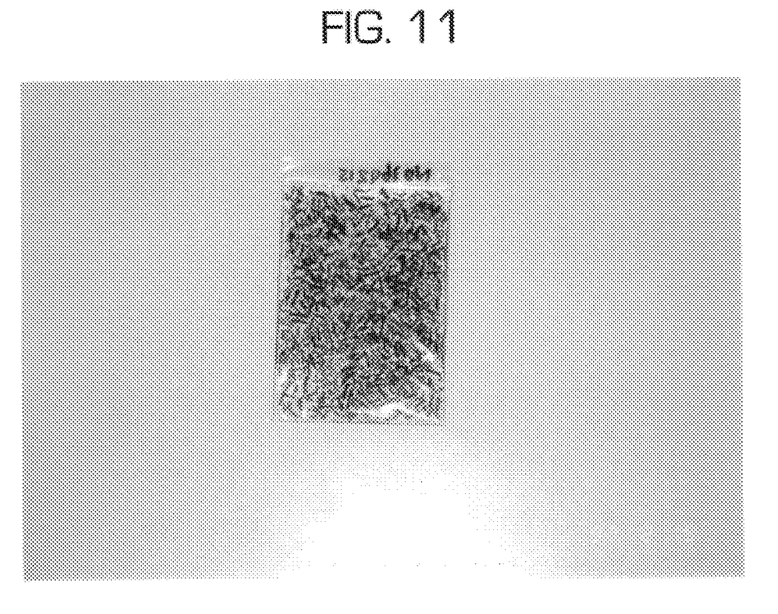
FIGS. 11 and 12 are morphological photos comparing the composition C (FIG. 11) equivalent to that observed immediately after the start of the test and the composition C (FIG. 12) observed one year later.
Figure 12:
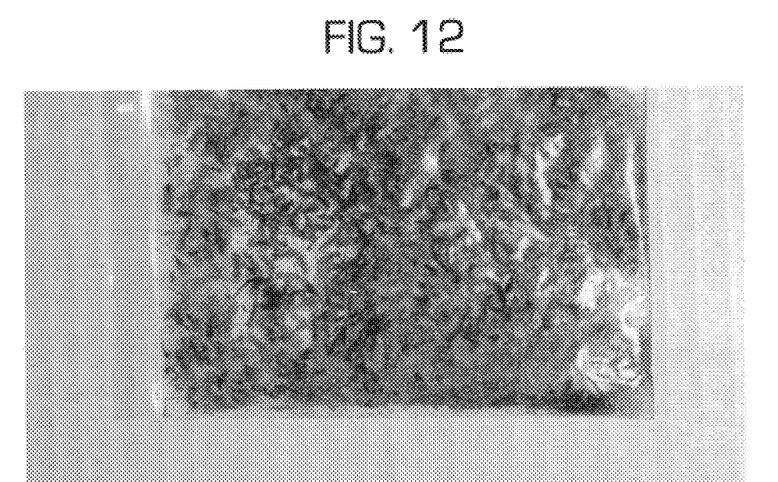

FIGS. 11 and 12: Morphological photos comparing the composition C (FIG. 11) equivalent to that observed immediately after the start of the test and the composition C (FIG. 12) observed one year later. The composition C in FIG. 11 was manufactured at the end of the test under conditions identical to those at the beginning of the test.

As seen from the test results, the high-viscosity composition of the invention serves as an excellent carrier for fixing a "plant capable of growing in the presence of at least water and light" therein and is quite useful for the aforementioned applications.

(4) Composition D of the Invention

Figure 13:
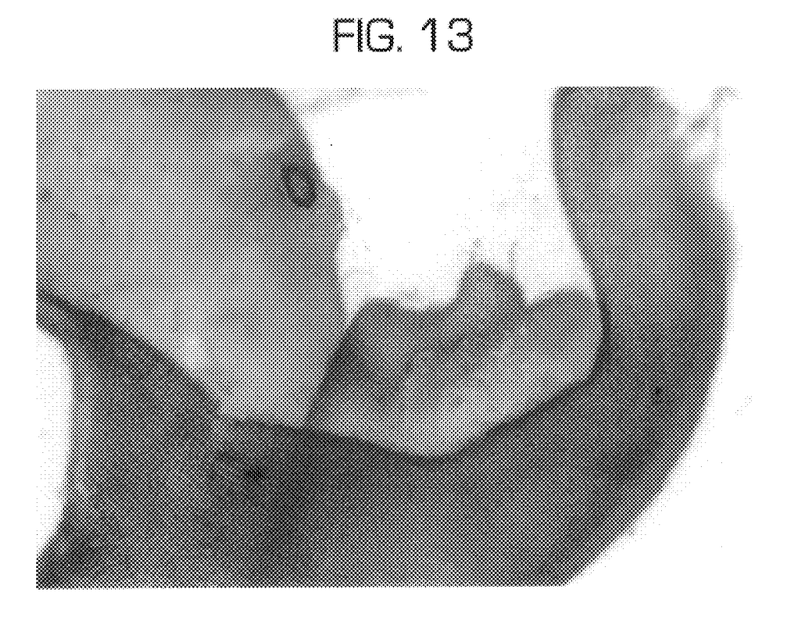
FIG. 13 is a morphological photo showing the growth of green laver contained in the composition D as observed through an optical microscope one year later.

One year after manufacture, even though the composition D showed a slight reduction in the amount of water contained in the gel, the green laver contained in the composition D was far from becoming weak; growth of the green laver was observed. (FIG. 13 is a morphological photo showing the growth of the green laver contained in the composition D as observed through an optical microscope one year later.)

As seen from the test results, the high-viscosity composition of the invention manufactured through contact with seawater serves as an excellent carrier for fixing seaweed therein and is quite useful for the aforementioned applications.

TEST EXAMPLE 2

Plant Cultivation Test of the Low-Viscosity Compositions of the Invention

Compositions E, F, and G of the invention contained in respective test tubes were allowed to stand in the room for one year with no external force, such as vibration, being applied.

After one year, the compositions E and F assumed a darker green color than at the beginning of the test, and the composition G showed the growth of individual fragments of plant bodies of *Rhacomitrium canescens* (Hew.) Brid.

Further, after one year, the compositions E, F, and G sustained conditions similar to those observed at the beginning of the test. Specifically, the contained plant elements did not exhibit deposition on the bottoms of the test tubes, adhesion to the test tube walls, or floating on the hydrogel aggregates, and sustained the uniformly dispersed state in the systems contained in the respective test tubes.

Figure 14:
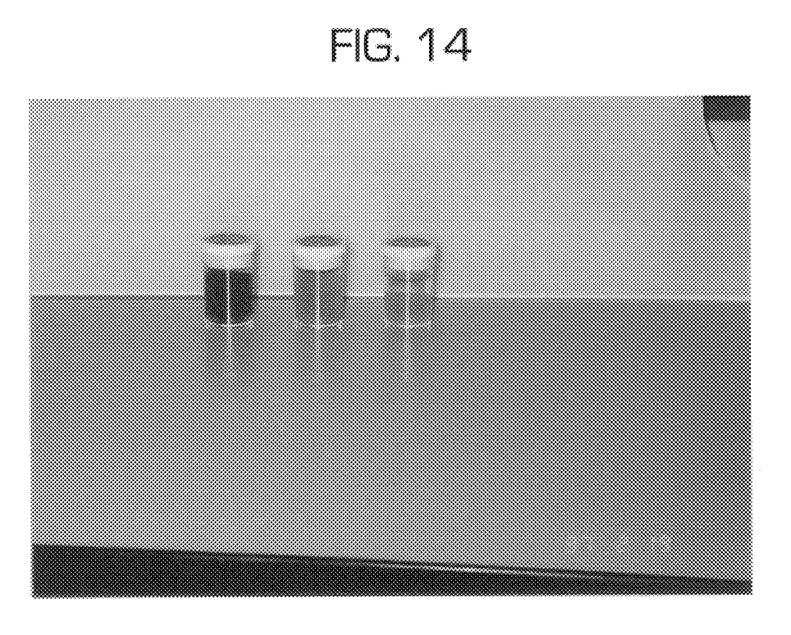
FIG. 14 is a photo showing the morphology of the compositions E, F, and G as observed at the end of a plant cultivation test.

FIG. 14: A photo showing the morphology of the compositions E, F, and G as observed at the end of the test. In this photo, the composition G is located on the left, the composition E is located in the center, and the composition F is located on the right. As seen from this photo, the compositions show sound growth and uniform dispersion. The transparent portion observed in the test tube containing the composition F is excess water derived from a relatively large amount of water being brought into contact with GX-205. In the test tube, the lower hydrogel aggregate shows the uniform dispersion of the protonema of *Rhodobryum giganteum* (Schwaegr.) Par.

As seen from the test results, the low-viscosity compositions of the invention serve as an excellent carrier for fixing a "plant capable of growing in the presence of at least water and light" therein in the form of a uniformly dispersed system and are quite useful for the aforementioned applications.

EXAMPLE 8

Manufacture of a Revegetation Material Through use of *Rhacomicrium canescens* (Hew.) Brid.

Cultivated *Rhacomitrium canescens* (Hew.) Brid. were cut at a portion located 3–8 mm from the top caulis to obtain fragments of the plant bodies. The fragments of plant bodies of *Rhacomitrium canescens* (Hew.) Brid. were washed well in water and were used as a moss to be dispersed within a gel aggregate.

40 ml of water were brought into contact with 1.7 g of NA-010 (trade name of a product manufactured by Showa Denko K.K.) to obtain a high-viscosity gel aggregate. 32 g of the above fragments of plant bodies of *Rhacomitrium canescens* (Hew.) Brid. were mixed into the obtained gel aggregate to obtain a composition. The thus-obtained composition was filled into an airtight bag having packing (trade name: UNIPACK; manufactured by Seinichi Co., Ltd.). The bag was then hermetically sealed. Through use of a knife, 5 cuts were formed in one side wall of the bag.

Subsequently, the bag was allowed to stand in an indoor site, which was shady place at all times, for 3 months with the cuts facing upward.

As a result, there was created the basic form of a revegetation material in which plant bodies of *Rhacomitrium canescens* (Hew.) Brid. grew and intertwined.

The gel aggregate in which plant bodies of *Rhacomitrium canescens* (Hew.) Brid. intertwined was removed from the bag. Then, the gel aggregate was washed off with city water to obtain a desired revegetation material of the invention having a substrate form.

Subsequently, the revegetation material was sun-dried and subjected to the cultivation test described in Test Example 3.

TEST EXAMPLE 3
Moss Cultivation Test Applied to the Revegetation Material

Through use of pressure sensitive adhesive double coated tape, the revegetation material manufactured in Example 8 was attached onto a sunny concrete wall which had been constructed 3 years or more before the test. City water was sprinkled over the revegetation material 4 times a day for one month. As a result, regeneration of blastemas was observed with the revegetation material; thus, sprinkling of water was terminated so that the revegetation material was watered only by natural precipitation.

After 3 months from the beginning of the test, the plant bodies of *Rhacomitrium canescens* (Hew.) Brid. of the revegetation material were found to have grown to 1 cm to form a moss community.

What is claimed is:

1. A composition consisting essentially of an autotroph, an N-vinylcarboxylic amide polymer, said polymer being formed from at least 70% by weight N-vinylcarboxylic amide monomer and being a cross-linked insoluble polymer, and a major amount of water, said polymer and said water forming a hydrogel aggregate.

2. The composition according to claim 1, wherein the autotroph is dispersed.

3. The composition according to claim 1, wherein the autotroph is at least one selected from the group consisting of algae, Bryophyta and Lichenes.

4. The composition according to claim 3, wherein the algae is a freshwater algae.

5. The composition according to claim 3, wherein the algae is a seawater algae and the water is seawater.

6. The composition according to claim 1, wherein said polymer is contained in a hydrogel aggregate-forming amount.

* * * * *